(12) United States Patent
Hellum

(10) Patent No.: US 12,263,078 B1
(45) Date of Patent: Apr. 1, 2025

(54) CUSTOMIZED DERMATOME FOR SKIN GRIFT TRANSPLANTATION

(71) Applicant: The United States of America as represented by the Secretary of the Navy, Newport, RI (US)

(72) Inventor: Aren M Hellum, Wakefield, RI (US)

(73) Assignee: The United States of America as represented by the Secretary of the Navy

( * ) Notice: Subject to any disclaimer, the term of this patent is extended or adjusted under 35 U.S.C. 154(b) by 874 days.

(21) Appl. No.: 17/471,245

(22) Filed: Sep. 10, 2021

(51) Int. Cl.
*A61F 2/10* (2006.01)
*B33Y 50/00* (2015.01)
*B33Y 80/00* (2015.01)

(52) U.S. Cl.
CPC .............. *A61F 2/105* (2013.01); *B33Y 50/00* (2014.12); *B33Y 80/00* (2014.12); *A61F 2240/00* (2013.01); *A61F 2240/002* (2013.01)

(58) Field of Classification Search
CPC ........................... B33Y 50/00; A61F 2240/002
See application file for complete search history.

(56) References Cited

U.S. PATENT DOCUMENTS

| | | | | |
|---|---|---|---|---|
| 2016/0137979 | A1* | 5/2016 | Tumey | C12N 5/0698 435/395 |
| 2016/0221206 | A1* | 8/2016 | Jeske | B26D 7/2614 |
| 2017/0274562 | A1* | 9/2017 | Tumey | B33Y 80/00 |
| 2019/0015548 | A1* | 1/2019 | Harrell | A61L 27/3604 |
| 2019/0059924 | A1* | 2/2019 | Sjöberg | A61B 17/322 |
| 2022/0296424 | A1* | 9/2022 | Prabhakar | B33Y 50/00 |

OTHER PUBLICATIONS

Ding, Houzhu, et al. "Design of a skin grafting methodology for burn wound using an additive biomanufacturing system guided by hyperspectral imaging." International Manufacturing Science and Engineering Conference. vol. 49903. American Society of Mechanical Engineers, 2016. (Year: 2016).*
Lee, Jian-Yuan, Jia An, and Chee Kai Chua. "Fundamentals and applications of 3D printing for novel materials." Applied materials today 7 (2017): 120-133. (Year: 2017).*
Warner, John, et al. "Design and 3D printing of hydrogel scaffolds with fractal geometries." ACS Biomaterials Science & Engineering 2.10 (2016): 1763-1770. (Year: 2016).*

* cited by examiner

*Primary Examiner* — Darrin D Dunn
*Assistant Examiner* — Vi M Tran
(74) *Attorney, Agent, or Firm* — James M. Kasischke; Michael P. Stanley; Jeffry C. Severson

(57) ABSTRACT

A customized dermatome skin graft transplantation system is provided and configured to photograph a trauma wound using a photo-optical digital imaging device to digitize an image, to determine a spatial coordinate pattern from the digital photographic image representing an ideal skin graft shape customized to the photographed trauma wound, and to operate a computer-controlled three-dimensional printer to manufacture a dermatome customized to the spatial coordinate pattern for placement on donor skin or a polymeric material to act as a guide for the cutting of a graft flap. The skin graft flaps are customized to the shape of the trauma wound to increase the resultant perimeter-to-area ratio of the surgically applied graft, with associated healing and aesthetic benefits. Computer-assisted embodiments of the present invention can incorporate image processing and/or artificial intelligence elements.

1 Claim, 5 Drawing Sheets

CUSTOMIZED DERMATOME FOR SKIN GRIFT TRANSPLANTATION

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER APPLICATIONS

None.

BACKGROUND OF THE INVENTION

(1) Field of the Invention

The present invention relates generally to skin grafting technology and more particularly to a system and associated method for the harvesting of skin graft for surgical transplantation to a wound area.

(2) Description of the Related Art

Medical practitioners require effective treatments for trauma to human or animal skin. Skin can be traumatized by burns, lacerations, incisions, tears, punctures, ulcerations, abrasions, lesions, animal bites, surgery and other causes. While some skin trauma may heal without medical treatment, other skin trauma will not; thereby, creating a need for skin graft transplantation.

Immunologically, a preferred type of skin graft transplantation is an autologous graft method in which a graft is taken from another area of the body of a patient to minimize a negative immune reaction. Known methods for obtaining a skin graft are typically variations of slicing through healthy skin to obtain a graft flap of skin suitable for attaching to the targeted trauma area. The slice is taken with a surgical device known as a dermatome. A dermatone is a cutting surface mounted in a razor holder that can remove skin from a skin area.

Skin taken from the donor site is usually rectangular. Once taken, the graft flap may be subjected to numerous slices which have the aggregate effect of making the graft stretchable and flexibly formable. This slicing, also known as meshing, of the graft provides the advantage of flexibly fitting the graft flap to the trauma site and allowing the passage of fluid from the surgery site during healing. However, meshing also increases the possibility of infection and can leave the healed skin at the donor site with a pebbled surface texture.

Another problem with known grafting methods that start with a rectangular graft flap is poor tissue healing. For example, when a graft is harvested in the shape of a rectangle but the trauma wound site is not similarly rectangular; then the graft process removes more healthy tissue from a donor site than is required to treat the wound. Doing so may not only represent needless trauma but also may result in unwanted scarring at the enlarged treatment site. Although the acceptance of a graft and suitable healing increases as the ratio of a graft perimeter to a graft surface area increases; a rectangular graft flap presents the lowest possible ratio of graft perimeter length to graft surface area.

As such, a need exists for practical customization of the shape of a skin graft to the shape of the trauma wound.

BRIEF SUMMARY OF THE INVENTION

Accordingly, it is a primary object and general purpose of the present invention to provide a dermatome skin graft transplantation system having a digital photographic imaging module, a spatial coordinate processing module, and an additive manufacturing module.

In use, the digital photographic imaging module captures an image of a wound site. The spatial coordinate processing module creates a set of spatial coordinates calculated from output data of the digital photographic imaging module. The additive manufacturing module creates instructions for operating an additive manufacturing means wherein the instructions reflect the output data of the spatial coordinate processing module.

The additive manufacturing means creates a graft stencil die defining a pattern complementary to the image captured by the digital photographic imaging module. The stencil die guides a dermatome to slice donor material in order to produce a graft flap in the stencil die pattern for surgical attachment to the wound site.

The digital photographic imaging module may control a digital camera. In use, the digital image of the trauma is retrieved for processing by the spatial coordinate processing module (optionally implemented using artificial intelligence), which generates the spatial coordinates that define a shape that is complementary to the shape of the trauma. The spatial coordinates are received by the additive manufacturing module, which processes the coordinates to create instructions for operating an additive manufacturing means (for example, a three-dimensional printer).

Using the received coordinates, the printer manufactures the graft stencil die. The graft stencil die produces a border that defines a shape complementary to the shape of the trauma wound. The resulting stencil die is placed on the surface of donor skin (preferably of autologous tissue or of a graft synthetic material) and depressed to cause raising of the skin or material. The raised skin defines a shape complementary to the pattern generated by the spatial coordinate processing module. The raised skin is positioned relative to the perimeter of the stencil die such that the skin is subsequently sliced through by a blade of a dermatome to result in a slice of skin that is complementary to the shape determined by the spatial coordinate calculation module.

The spatial coordinate processing module calculates coordinates in two or three dimensions. The module calculates the coordinates that define the boundary of a geometric fractal pattern. Geometric fractal pattern, as used herein, refers to an irregular, geometric shape of linear, curved, or curvilinear segments where the geometric shape is characterized by inlets, indentations, recesses, and/or notches.

An advantage in calculating the geometric fractal pattern is that, with the property of numerous indentations and recesses, the ratio of perimeter length to surface area increases; thereby, increasing the acceptance and healing of the grafted tissue or material. Although the ratio of perimeter length to the surface may be increased by a regular pattern of indentations, one object of the present invention is to create a graft flap which can cover an irregular surface.

The additive manufacturing module facilitates operational control of a three-dimensional printer by translating the wound site coordinates into instructions for printing, layering, and/or depositing a polymer or a metal into a final shape that conforms to a set of coordinates where the final shape of the object being so printed forms a graft stencil die whose perimeter shape is the determined perimeter shape.

Slicing the skin into a graft flap whose perimeter shape is substantially the same as the determined shape includes: positioning the graft stencil die onto donor or synthetic material; forcing the skin or material upwards by pressing down on the stencil die; and then passing a dermatome blade over the guide fence formed by the stencil die. The graft flap is then surgically attached to the tissue.

In an alternative embodiment of the present invention, a digital picture is taken of the wound site. Using a guided scissors computer routine; a practitioner makes a digital outline of the wound. A graft pattern is generated with a high perimeter-to-area ratio that remains inside the wound outline. This pattern generation step takes place on the computer used to process the image of the wound using a pattern generation module. The outline of the graft pattern is converted to the machine code needed to create the dermatome stencil.

If the stencil is manufactured using additive techniques; the translation first goes to slicing software used by the printer, which performs the necessary conversion to machine code. The stencil is produced by cutting or additive manufacturing; thereby, resulting in a stencil or stencil die that is affixed to the graft removal site.

One example of fixation is by adherence at the stencil edges with heavy tape. A self-adhesive stencil material may be used for relatively larger graft removal sites. The graft is then removed using a dermatome and put in place on the wound site.

The printing means may include a three-dimensional metal or polymer deposition printer selected from the group consisting of metal extrusion, vat polymerization, material jetting, binder jetting, powder bed fusion printing, selective laser melting, direct metal laser sintering, electron beam melting and ultrasonic additive manufacturing printers.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein like reference numerals and symbols designate identical or corresponding parts throughout the several views and wherein.

DETAILED DESCRIPTION OF THE INVENTION

Figure 1:
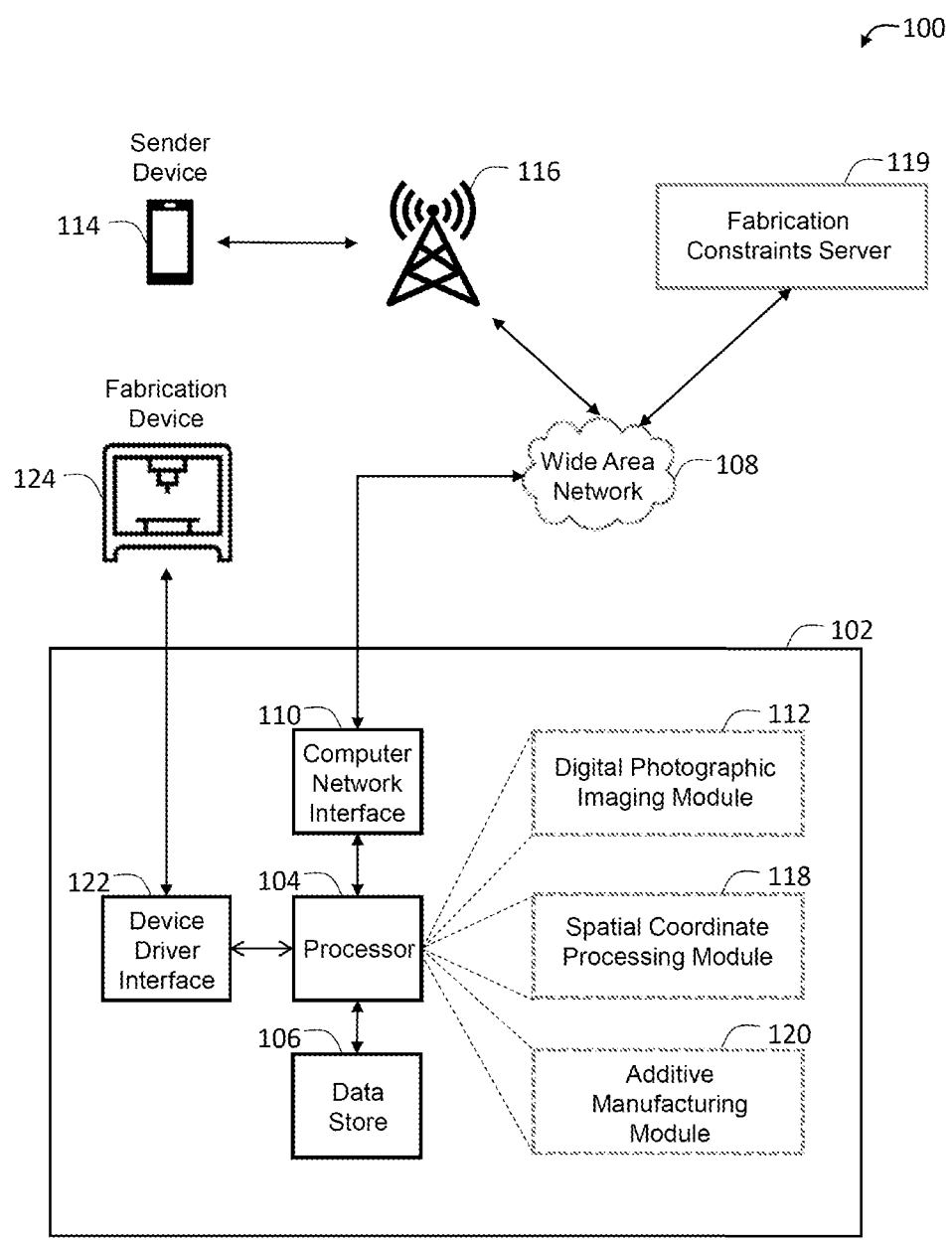
FIG. 1 depicts a schematic diagram of a customized dermatome skin graft transplantation system of the present invention.

FIG. 1 depicts a customized dermatome skin graft transplantation system 100. A dermatome customization host 102 includes a processor 104 that executes computerized instructions. A data store 106 stores data and instructions used by the processor 104. Specifically, the processor 104 is in data communication with networked devices and directs input from the devices to the data store 106 for storage and retrieval.

In the figure, the processor 104 is in data communication with external computing resources, such as a wide area network 108, through a computer network interface 110. Furthermore, the processor 104 directs input received from components of the wide area network 108 to the data store 106. Similarly, the processor 104 retrieves data from the data store 106 to be forwarded as output to the wide area network 108.

The instructions of the customized dermatome skin graft transplantation system 100 that implements a digital photographic imaging module 112 are stored in the data store 106 and retrieved by the processor 102. The digital photographic imaging module 112 receives and interprets data reflecting an image representation of a wound site. The digital photographic imaging module 112 receives signals originating from a sender device 114. The sender device 114 may be a camera app to capture image data and to transmit the image data over a network 116 and/or the wide area network 108 to the computer network interface 110 of the dermatome customization host 102. One advantage of the digital photographic imaging module 112 is that the module receives imaging data originating from any sender device 114 capable of transmitting photo-optical images.

The dermatome skin graft transplantation system 100 implements a spatial coordinate processing module 118 that is stored in the data store 106 and retrieved by the processor 104 for execution. The spatial coordinate processing module 118 analyzes the digital image of the wound site and determines spatial coordinates defining a shape substantially matching the wound site. The spatial coordinate processing module 118 exchanges information regarding additional variables (described below as fabrication constraints) to be applied along with the image data when calculating the spatial coordinates.

For example, the dermatome customization host 102 is in data communication with one or more fabrication constraint servers 119 to exchange fabrication constraints data that augments the digital image data provided by the digital photographic imaging module 112.

The instructions of the customized dermatome skin graft transplantation system 100 that implement an additive manufacturing module 120 are stored in the data store 106 and retrieved by the processor 104. The additive manufacturing module 120 interprets the spatial coordinates to create additive manufacturing instructions communicated through a device driver interface 122 to a fabrication device 124. When executed, the additive manufacturing instructions operate the fabrication device 124 to create a graft stencil die having a pattern complementary to the wound site image. The graft stencil die guides slicing of a donor material to produce a graft flap in the pattern of the stencil die that is suitable for attachment.

Figure 2:
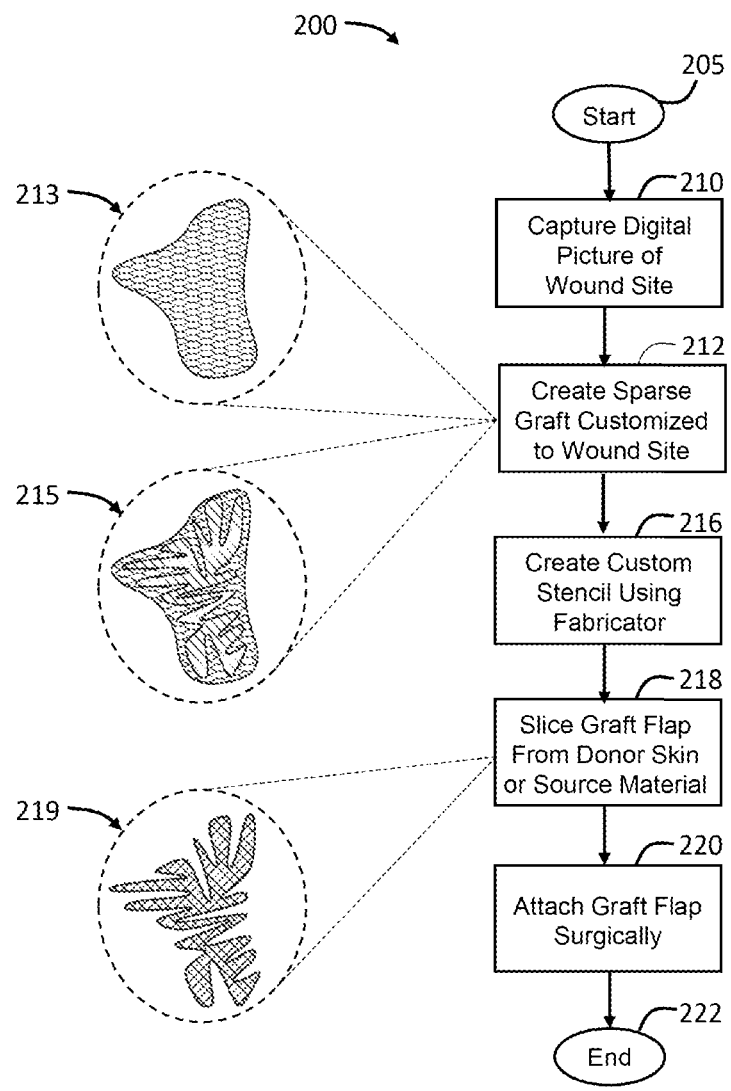
FIG. 2 depicts a flow chart of exemplary steps of a customized dermatome skin graft transplantation method of the present invention.

Referring now to FIG. 2, and continuing to refer to FIG. 1, a block diagram 200 illustrates the operation of the computer-assisted aspects of the present invention. From a start at Block 205, the digital photographic imaging module 112 captures the image of the trauma to be treated (Block 210). The digital photographic image is received by the spatial coordinate processing module 118 that, at Block 212, creates a graft that is designed to coarse dimensions 213 and detailed contours 215 of the wound site.

The graft is a geometric substantially fractal pattern having indentations to increase a perimeter length while keeping the pattern within the confines of the image of the wound site. A blade stencil or stencil die is created using operation instructions determined by the additive manufacturing module 120 (Block 216) to drive the fabrication device 124.

The stencil and/or stencil die is configured for positioning over an area of donor skin or an area of synthetic skin graft material for pushing downward to cause the skin to rise above the rim of the stencil or die with sufficient height for a cutting profile. At Block 218, this cutting profile guides a slicing action of a dermatome blade that runs against the rim as a cutting jig; thereby, slicing the donor skin or synthetic material into a flap graft 219 that has the desired shape for attachment to the wound (Block 220). Completion of the attachment operation and the skin graft transplantation method ends at Block 222.

Figure 3:
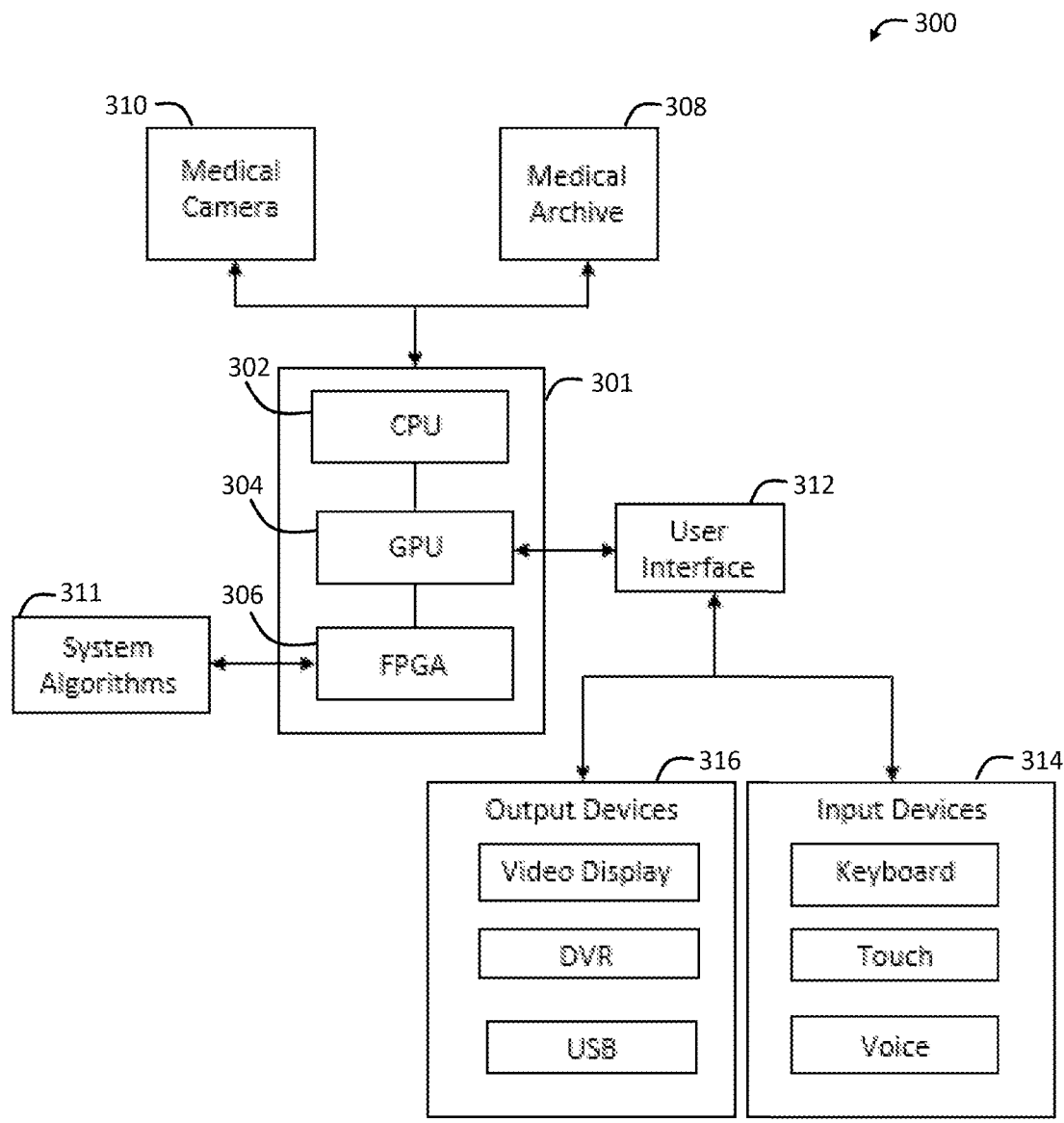
FIG. 3 depicts a schematic block diagram illustrating an exemplary computer processing system configured to host components of the customized dermatome skin graft transplantation system and computer-assisted method of FIG. 1 and FIG. 2.

Referring now to FIG. 3 and continuing to refer to FIG. 1; a computer processing system 300 executes various features of the present invention. For example, the processing system 300 implements the digital photographic imaging module 112 and includes processor elements 301 such as a central processing unit (CPU) 302, a graphics processing unit (GPU) 304, and/or a field programmable gate array (FPGA) 306. The processing system 300 retrieves and processes data derived from a medical archive 308 or a surgical camera 310. The camera 310 and/or medical archive 308 transmit a data stream to the central processing unit 302. The field programmable gate array 306 simultaneously processes the data by using one or more programmed system algorithms 311; thereby, functioning as an image clarifier within the processing system 300.

The graphics processing unit 304 communicates with a user interface 312 which displays the data from the medical archive 308 and/or the medical camera 310. The graphics processing unit 304 enables the user interface 312 to communicate the data to the input devices 314 and/or output devices 316. In embodiments of the present invention, the user interface 312 simultaneously communicates to multiple input devices 314 and output devices 316.

Figure 4:
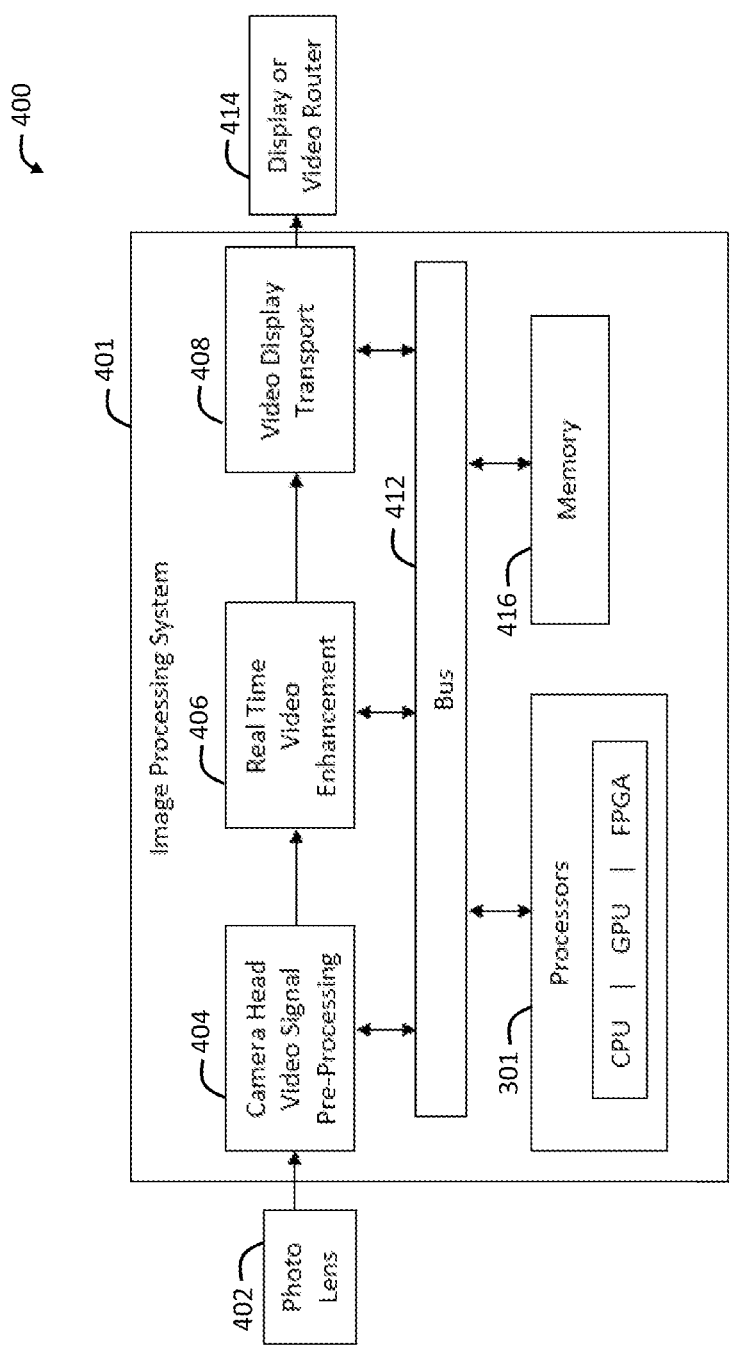
FIG. 4 depicts a schematic block diagram illustrating an exemplary image processing system configured to host components of the customized dermatome skin graft transplantation system and computer-assisted method of FIG. 1 and FIG. 2.

Referring now to FIG. 4, and continuing to refer to FIG. 1 and FIG. 3, a schematic diagram 400 illustrates an image processing system 401. The image processing system 401 implements the spatial coordinate processing module 118 and processes image data received from a photo lens 402. The image processing system 401 includes a camera head video pre-processing component 404, a real time video enhancement component 406 and a video display transport component 408.

Image data captured by the photo lens 402 transmits to the camera head video pre-processing component 404. Image pre-processing may also include software modules for image registration and segmentation to optimize the video data and communicate via a system bus 412. The pre-processed image data transmits to the video enhancement component 406; whereby, the image data is enhanced to improve clarity.

After the image data resolution has been enhanced, the video display transport component 408 completes image post-processing; formatting from the initial sensor resolution to the display resolution (e.g., enhancing the video data display resolution or using software modules such as video cross conversion, scaling and adding graphic overlays). The processed image data is then transmitted from the image processing system 401 to a display or video router 414. The video display transport 408 saves the processed image data to a processing system memory 416.

Figure 5:
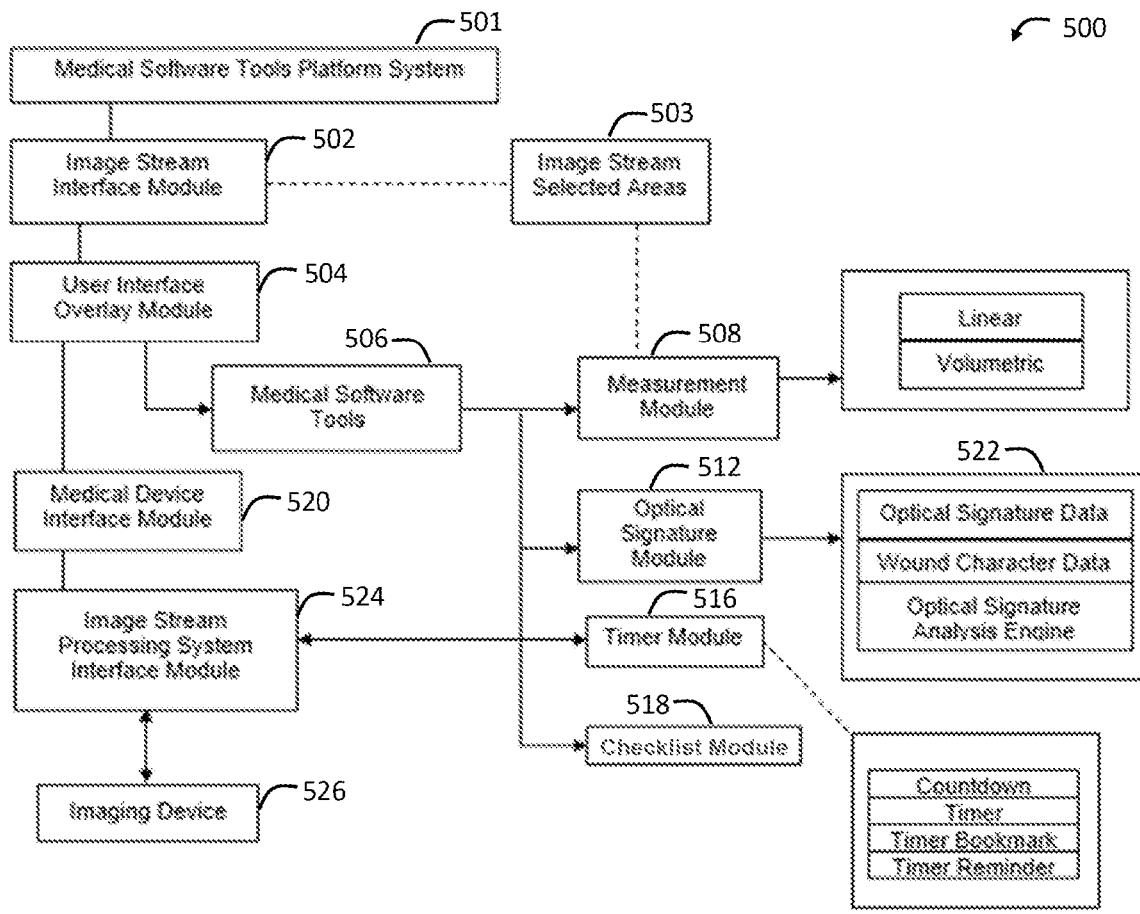
FIG. 5 depicts a schematic block diagram illustrating an exemplary medical imaging module configured to implement digital photographic imaging logic of the customized dermatome skin graft transplantation system and computer-assisted method of FIG. 1 and FIG. 2.

Referring now to FIG. 5, and continuing to refer to FIG. 1 and FIG. 3, a schematic diagram 500 depicts an exemplary medical software platform system 501 implementing the present invention. The platform system 501 may implement one or more of the digital photographic imaging module 112, the spatial coordinate processing module 118 or the additive manufacturing module 120.

The medical software tools platform system 501 receives an image stream of an area of traumatized skin tissue from an image stream interface module 502. An area of a selected overall image stream 503 is utilized within a user interface overlay module 504, which includes one or more graphical user interface elements presented over the image stream received through the image stream interface module 502. The user interface overlay module 504 enables communication between the medical software tools platform system 501 and one or more medical software tools 506, such as a measurement module 508, an optical signature module 512, a timer module 516, and a checklist module 518. A medical device interface module 520 facilitates communication between the medical software tools platform system 501 and one or more of the medical software tools 506. An image stream processing system interface module 524 interfaces with the timer module 516 and an imaging device 526.

The measurement module 508 facilitates measurement of one or more anatomical structures presented in an image stream received through the image stream interface module 502. The measurement module 508 also enables a user to select a region in the image stream 503 and to determine a measurement based on the region. The measurement may include linear measurements and volumetric measurements of an anatomical structure or tissue.

The optical signature module 512 facilitates the processing of the signature data 522 such as optical signature data, wound character data and an optical signature analysis engine. The timer module 516 facilitates the addition of one or more countdown timers, clocks, stopwatches, alarms, or the like, that may be added and displayed over the image stream 503 through the user interface provided by the user interface overlay module 504. For example, the timer module 516 may allow a user (e.g., surgeon) to add a countdown timer in association with a surgical step (e.g., clamping of an artery).

Manufacturing aspects of the present invention utilize three-dimensional printing in delivering multiple outcomes. An alternative to polymer three-dimensional printing; metal three-dimensional printing (including Selective Laser Melting and Direct Metal Laser Sintering) is known to provide advantages when used to create end-use engineering products.

System aspects of the present invention may utilize an artificial intelligence (AI) framework in addressing and delivering outcomes. For example, AI may be employed to determine geometric substantially fractal skin graft flap shapes.

Also, a system aspect of the invention provides an environment for understanding and predicting the consequences of treatment choices. Such simulation modeling may improve decision making as well as a fundamental understanding of the healthcare system and clinical process by playing out potential scenarios. The AI framework provides the basis for clinical artificial intelligence that may deliberate in advance, form contingency plans to cope with uncertainty and adjust to changing information.

Artificial Intelligence fabrication constraints can account for graft characteristics including variables that inform the user to deviate from the wound shape to instead account for donor characteristics such as graft location, graft age, graft temperature, graft hydration, graft source, graft thickness, and/or graft meshing. The fabrication constraints may also account for fabricator characteristics including variables that inform the user to deviate from the wound shape to instead account for mechanical limitations, material limitations, cost limitations, time limitations, and/or standards of care limitations.

An autonomous AI software means may reside within patient monitoring computation devices and/or within doctor assisting computation devices. Information from patient monitoring is communicated to the assisting devices and can influence the doctor through a recommendation and/or a change in the treatment decisions of the doctor. Such AI software then analyzes these treatment decisions and can deliver updated patient-outcome prediction results. Such patient-monitoring and doctor-assisting computation devices function as communication devices to web-based AI software that can perform the analysis. Databases of information help the doctor-assisting computation devices, such as electronic health records, personal history records, and genetic marker records.

Alternatively, an implementer may construct a more specialized apparatus to perform the method steps, such as a Picture Archiving and Communication System (PACS). PACS provides medical imaging technology for storage of, and convenient access to images from multiple source machine types. Electronic images and reports are transmitted digitally via PACS; thereby, eliminating the need to manually file, retrieve, or transport film jackets. The format for PACS image storage and transfer is Digital Imaging and Communications in Medicine (DICOM).

The foregoing description of the preferred embodiments of the invention has been presented for purposes of illustration and description only. It is not intended to be exhaustive nor to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. A customized dermatome skin graft transplantation system comprising:
a wide area network which communicates with at least one fabrication constraint server;
a sender device which captures a wound site image from a wound site and transmitting signals of the wound site image over said wide area network;
a digital photographic imaging module operationally connected to and which receives the signals from said wide area network and interpreting data reflecting the wound site image with data of fabrication constraints provided by the at least one fabrication constraint server;
a data store;
a spatial coordinate processing module in said data store with said spatial coordinate processing module operationally connected to said digital photographic imaging module wherein said spatial coordinate processing module analyzes the wound site image as well as the fabrication constraints and determining a set of spatial coordinates to define a shape substantially matching the wound site and wherein said spatial coordinate processing module which is in data communication with said wide area network to direct input from said wide area network to said data store for storage and retrieval;
a three-dimensional metal deposition printer operationally connected to said spatial coordinate processing module for using the set of spatial coordinates and for using manufacturing instructions which are stored in said data store to create additive manufacturing instructions;
an additive manufacturing means operationally connected to said three-dimensional metal deposition printer, said additive manufacturing means which uses the additive manufacturing instructions to create a graft stencil die having a pattern substantially complementary to the wound site image;
wherein said graft stencil die is configured to guide slicing of donor material to produce a graft flap in a pattern of said graft stencil die and suitable for surgical attachment and wherein said graft stencil die is further configurable to be positionable on an area of skin defining a boundary of the donor material and to be compressed on the area of skin to present the donor material for surgical harvesting;
wherein the donor material is selected from a group consisting of an autologous tissue graft type and a synthetic skin graft material type;
wherein said spatial coordinate processing module is further operable to determine the set of spatial coordinates in two dimensions that comprise a geometric substantially-fractal pattern.

* * * * *